US009652845B2

(12) United States Patent
Rai et al.

(10) Patent No.: US 9,652,845 B2
(45) Date of Patent: May 16, 2017

(54) SURGICAL ASSISTANCE PLANNING METHOD USING LUNG MOTION ANALYSIS

(71) Applicant: Broncus Medical Inc., Mountain View, CA (US)

(72) Inventors: Lav Rai, Sunnyvale, CA (US); Jason David Gibbs, State College, PA (US); Henky Wibowo, Cupertino, CA (US)

(73) Assignee: BRONCUS MEDICAL INC., San Jose, CA (US)

( * ) Notice: Subject to any disclaimer, the term of this patent is extended or adjusted under 35 U.S.C. 154(b) by 0 days.

(21) Appl. No.: 14/696,889

(22) Filed: Apr. 27, 2015

(65) Prior Publication Data

US 2015/0228074 A1   Aug. 13, 2015

Related U.S. Application Data

(63) Continuation of application No. 13/107,471, filed on May 13, 2011, now Pat. No. 9,020,229.

(51) Int. Cl.
| | |
|---|---|
| *G06K 9/00* | (2006.01) |
| *G06T 7/00* | (2017.01) |
| *G06K 9/46* | (2006.01) |
| *G06T 7/20* | (2017.01) |
| *G06T 17/00* | (2006.01) |
| *G06T 7/246* | (2017.01) |
| *A61B 6/00* | (2006.01) |

(52) U.S. Cl.
CPC .............. *G06T 7/0012* (2013.01); *G06K 9/46* (2013.01); *G06T 7/20* (2013.01); *G06T 7/246* (2017.01); *G06T 17/00* (2013.01); *A61B 6/5264* (2013.01); *G06K 2009/4666* (2013.01); *G06T 2207/10076* (2013.01); *G06T 2207/30061* (2013.01)

(58) Field of Classification Search
None
See application file for complete search history.

(56) References Cited

U.S. PATENT DOCUMENTS

| | | | | |
|---|---|---|---|---|
| 7,356,367 | B2 * | 4/2008 | Liang ..................... | A61B 5/055 600/407 |
| 8,696,547 | B2 * | 4/2014 | Wibowo .............. | A61B 1/2676 600/109 |
| 2005/0135707 | A1 * | 6/2005 | Turek ....................... | G06T 7/38 382/294 |

(Continued)

*Primary Examiner* — Nancy Bitar
(74) *Attorney, Agent, or Firm* — Convergent Law Group LLP; Rick Batt

(57) ABSTRACT

A medical analysis method for estimating a motion vector field of the magnitude and direction of local motion of lung tissue of a subject is described. In one embodiment a first 3D image data set of the lung and a second 3D image data set is obtained. The first and second 3D image data sets correspond to images obtained during inspiration and expiration respectively. A rigid registration is performed to align the 3D image data sets with one another. A deformable registration is performed to match the 3D image data sets with one another. A motion vector field of the magnitude and direction of local motion of lung tissue is estimated based on the deforming step. The motion vector field may be computed prior to treatment to assist with planning a treatment as well as subsequent to a treatment to gauge efficacy of a treatment. Results may be displayed to highlight.

25 Claims, 7 Drawing Sheets

(56) References Cited

U.S. PATENT DOCUMENTS

| | | | |
|---|---|---|---|
| 2006/0079759 A1* | 4/2006 | Vaillant | A61B 6/12 600/424 |
| 2007/0015997 A1* | 1/2007 | Higgins | A61B 1/00009 600/407 |
| 2011/0058721 A1* | 3/2011 | Zhang | A61B 5/08 382/131 |
| 2012/0016269 A1* | 1/2012 | Moctezuma de la Barrera | A61B 19/5244 600/595 |
| 2012/0041291 A1* | 2/2012 | Ferren | A61B 1/041 600/365 |

* cited by examiner

US 9,652,845 B2

SURGICAL ASSISTANCE PLANNING METHOD USING LUNG MOTION ANALYSIS

CROSS-REFERENCE TO RELATED APPLICATIONS

None

FIELD OF THE INVENTION

The present invention relates to surgical procedures and in particular, to assisting physicians with planning surgical procedures in the lung.

BACKGROUND OF THE INVENTION

The use of computer generated 3D models of a patient's anatomy is well established. Such 3D models are based on real image data taken from the patient. The 3D models assist surgeons in planning a surgical procedure.

A number of commercially available systems process 3D image data sets of a patient and prepare a 3D model of the organ for the physician to review in advance of surgery. In some systems, virtual markers and regions of interests may be added or superimposed on the 3D model for review and adjustment by the physician. As example of such a planning system with application to the lung is the LungPoint® Planning System manufactured by Broncus Technologies, Inc. (Mountain View, Calif.).

A challenge with certain planning systems is to compensate for rhythmic or tidal motion of the organ arising from, e.g. breathing. An implant or anatomical feature positioned in the lung based on a 3D image of the lung in one state (e.g., full inspiration) may have a different position when the lung is in another state (e.g., full expiration). Failure to compensate for the displacement of the anatomy, implant, or device as the case may be could thwart the procedure and perhaps in some instances result in patient injury should the implant or device damage a vessel, pleural surface, or other sensitive region.

A number of techniques address to varying degrees of effectiveness the above mentioned challenge. For example, the paper entitled "Fast Deformable Registration on the GPU: A CUDA Implementation of Demons" by Pinar Muyan-Ozcelik, 2008 (hereinafter "The Muyan-Ozcelik paper") describes a deformable registration technique to map CT scans taken during expiration to CT scans taken during inspiration. However, amongst other things, the Muyan-Ozcelik paper does not appear to compensate for posture and position of the patient prior to deforming the CT images. Accordingly, more is required in order to accurately estimate a motion vector field of the magnitude and direction of local motion of a non-rigid organ such as the lung.

A method and system to assist surgeons to plan medical procedures with a wide variety of medical implements in a body organ, that has application to non-rigid organs such as the lung, and that does not suffer the above identified drawbacks is therefore desired.

SUMMARY OF THE INVENTION

One embodiment of the present invention is a method for assisting a surgeon to analyze the motion of a lung. Two 3D CT images are obtained as input. One 3D CT image represents the lung during a first state such as inspiration and a second 3D CT image represents the lung during a second state such as expiration. A rigid registration is performed between the two 3D CT images to align the images. The rigid registration is followed by a deformation until the two 3D CT images match. A motion vector field corresponding to the local motion of the lung to move from the first state to the second state is generated and output of the method.

In another embodiment of the present invention the motion vector field is displayed such that areas of greatest motion have the highest intensity.

In another embodiment of the present invention, efficacy of surgical treatments, or displacement of medical implements (such as devices, implants, and fiducials) may be computed and displayed based on a review of the motion vector field.

In another embodiment of the present invention, a second vector motion field is estimated following a treatment. The second vector motion field is compared to the first vector motion field to ideality regions of greatest change or to illustrate change in local motion of the lung tissue or the lack there of.

In another embodiment of the present invention an atlas motion vector field is created and stored. The atlas motion vector field is applied to a first 3D image data set of a patient such that the local motion of the lung tissue may be estimated based on the atlas motion vector field and the first 3D image data set.

In another embodiment of the present invention a system comprises a processor operable to estimate a motion vector field based on received image data as described herein.

In another embodiment, the system further includes a display which shows an animation of the motion of the lung and the displacement of a medical implement in the lung.

The description, objects and advantages of the present invention will become apparent from the detailed description to follow, together with the accompanying drawings.

BRIEF DESCRIPTION OF THE DRAWINGS

FIGS. 5-6 are same slices of CT images of a lung of a patient corresponding to inspiration and expiration respectively.

FIG. 8 is a CT image after performing a deformable registration on the CT image from FIG. 7 to register with the CT image of FIG. 6 such that the local lung structures align.

DETAILED DESCRIPTION OF THE INVENTION

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. It is to be appreciated that unless defined otherwise, all technical and scientific terms used herein have the same meaning as commonly understood by one of ordinary skill in the art to which this invention belongs.

Figure 1:
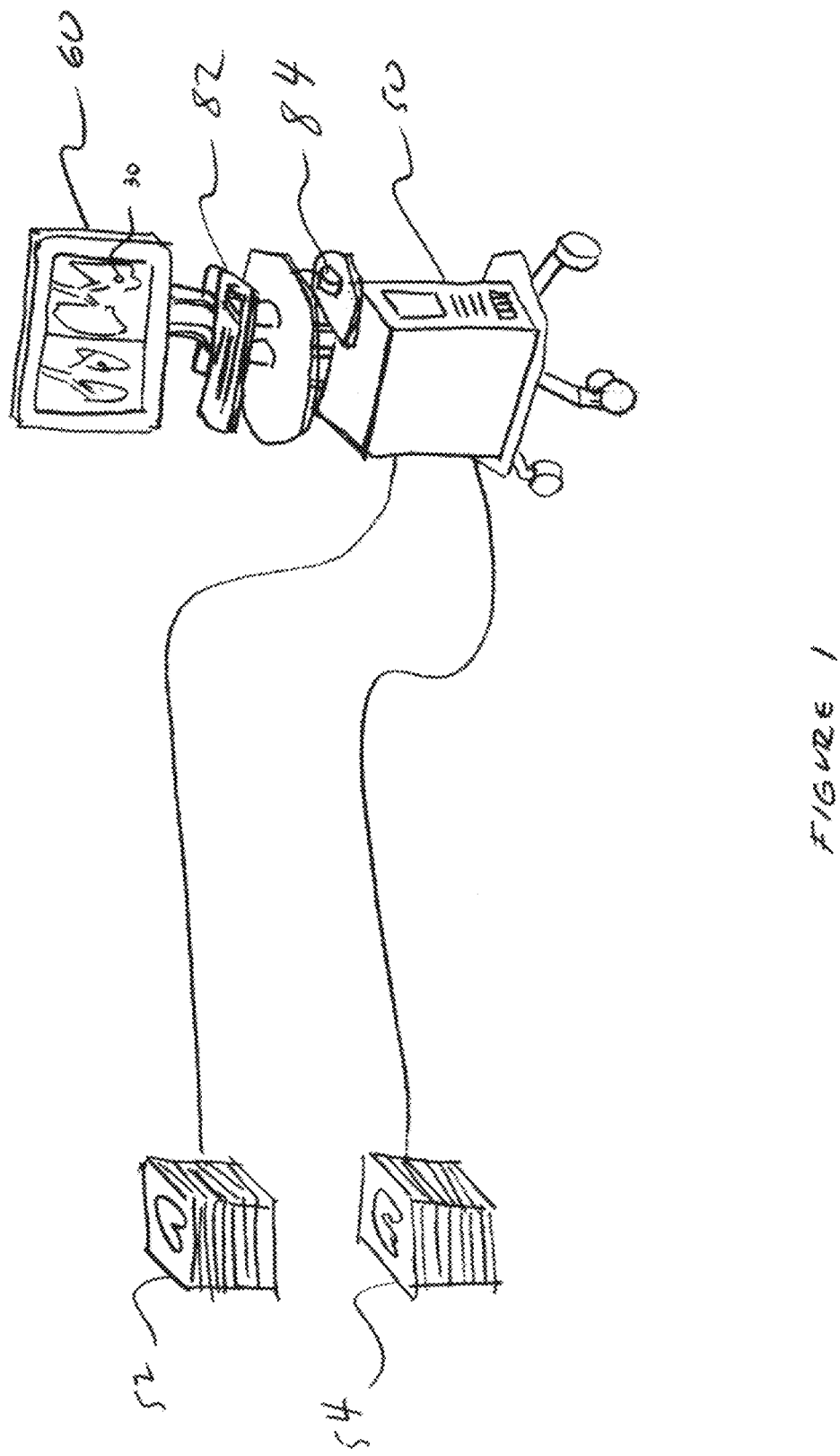
FIG. 1 is a schematic diagram of a workstation for performing a lung motion analysis for assisting a physician to plan a medical procedure.

FIG. 1 is an illustration of a system in accordance with one embodiment of the present invention. In particular, FIG. 1 illustrates a workstation 50 in communication with a first set of image data 52 and a second set of image data 54. The first set of image data and second set of data may correspond to, for example, 3D CT image data of the lung of a patient during inspiration and expiration respectively.

As will be described herein, the image data is received by the workstation and processed to compute or estimate a motion vector field of the lung which indicates local motion of the lung. The motion vector field may then be presented in various formats to the user on a display 60. As will be discussed further herein the user may insert a virtual medical implement 30 using a keyboard 82 and/or a mouse 84. The boundary, volume, and motion of the medical implement 30 may be computed based on the local motion vector field and displayed on monitor 60. The display may show the movement of the virtual medical implement to assist a physician to plan a surgical procedure.

Also, by "medical implement", it is meant to include but not be limited to implants and devices which may be used for treatment or diagnosis, and may be located in the subject permanently, or temporarily as the case may be. Examples of medical implements, without limitation, include implants, catheters, needles, ablation devices, stents, valves, fiducial markers, seeds, coils, etc.

Figure 2:
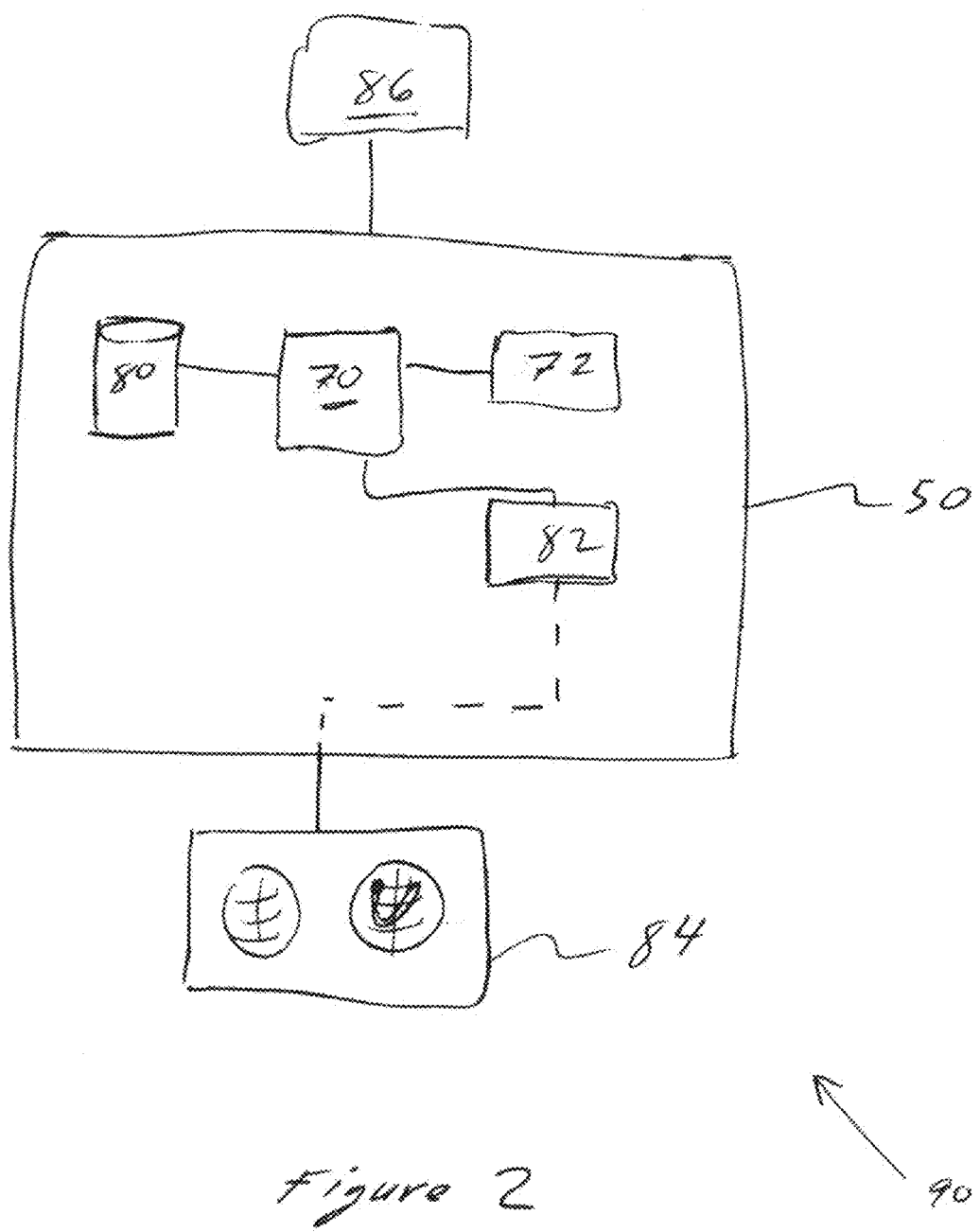
FIG. 2 is a block diagram of a lung analysis system in accordance with one embodiment of the present invention.

FIG. 2 illustrates a system 90 including a workstation or programmed computer 50. The workstation 50 shown in FIG. 2 includes a processor 70 operable to estimate the motion vector field of the lung based on, amongst other things, the multiple sets of 3D image data as will be described in more detail herein.

Workstation 50 is shown having a memory device 80 which holds or stores information including imaging, device, marker, and procedural data. The memory device may be a hard drive, for example. It is to be understood, however, that although the system in FIG. 2 is shown with a memory 80 for receiving and storing various information the invention is not so limited. In an alternative embodiment the system may be configured to merely access a memory device such as a USB stick, a CD, or other media storage device.

In another embodiment the processor is connectable to a memory device through the internet or through another communication line to access a network. For example, patient data CT scans may be stored on a server of a hospital and the processor of the present invention is adapted to access such data via a communication line and process the data. The workstation may communicate with the DICOM, for example, to receive such data sets.

The workstation 50 is adapted to send image data to a display 84 using a video card 82. An example of a workstation is a Dell Computer Model No. T5400, with Dual-core Intel Xeon 2.0 GHz processor, and a Nvidia Quadro FX 3800 video card. A frame grabber card 72 may optionally be provided to capture live video or image data as desired.

As mentioned above, the system 90 shown in FIG. 2 also includes a display 84 which may present reports, data, images, results and models in various formats including without limitation graphical tabular, animated, and pictorial form. Workstation 50 is configured to send to the display a number of types of images including 3D model views, 2D model fluoroscopy views, real fluoroscopy views, real endoscopic views, model endoscopic views, and a wide range of information superimposed on the views such as without limitation planning information, regions of interest, virtual target markers, vessels, virtual obstacles, real devices, virtual devices, routes to a target, notes and indicia provided by the user, etc. In one embodiment of the present invention, a medical implement is superimposed on a 3D model of the organ. In the case that planning information is to be utilized and or displayed, planning information may be provided or determined by the workstation as described in U.S. Patent Application No. 2008/0183073 to Higgins et al.

The system 90 shown in FIG. 2 also includes a user input device 86 such as, for example, a keyboard, joystick, or mouse. The user input device allows a user such as the physician to add or input data and information as well as modify planning information and to make notes in the files and records.

Displays may be incorporated with the processor in an integrated system (e.g., a lap top, tablet computer, or touch screen pad-type computer) or the displays may cooperate with the processor from a remote location. A processor may be adapted to send or deliver data across a network to one or more displays or portable computer devices or smart phones such as the iphone® manufactured by Apple, Inc. Cupertino, Calif., United States. Indeed, although the computer system 90 shown in FIG. 2 includes a number of various components incorporated into a system, the invention is not so limited. The invention is intended to be limited only as defined in the appended claims.

Figure 3:
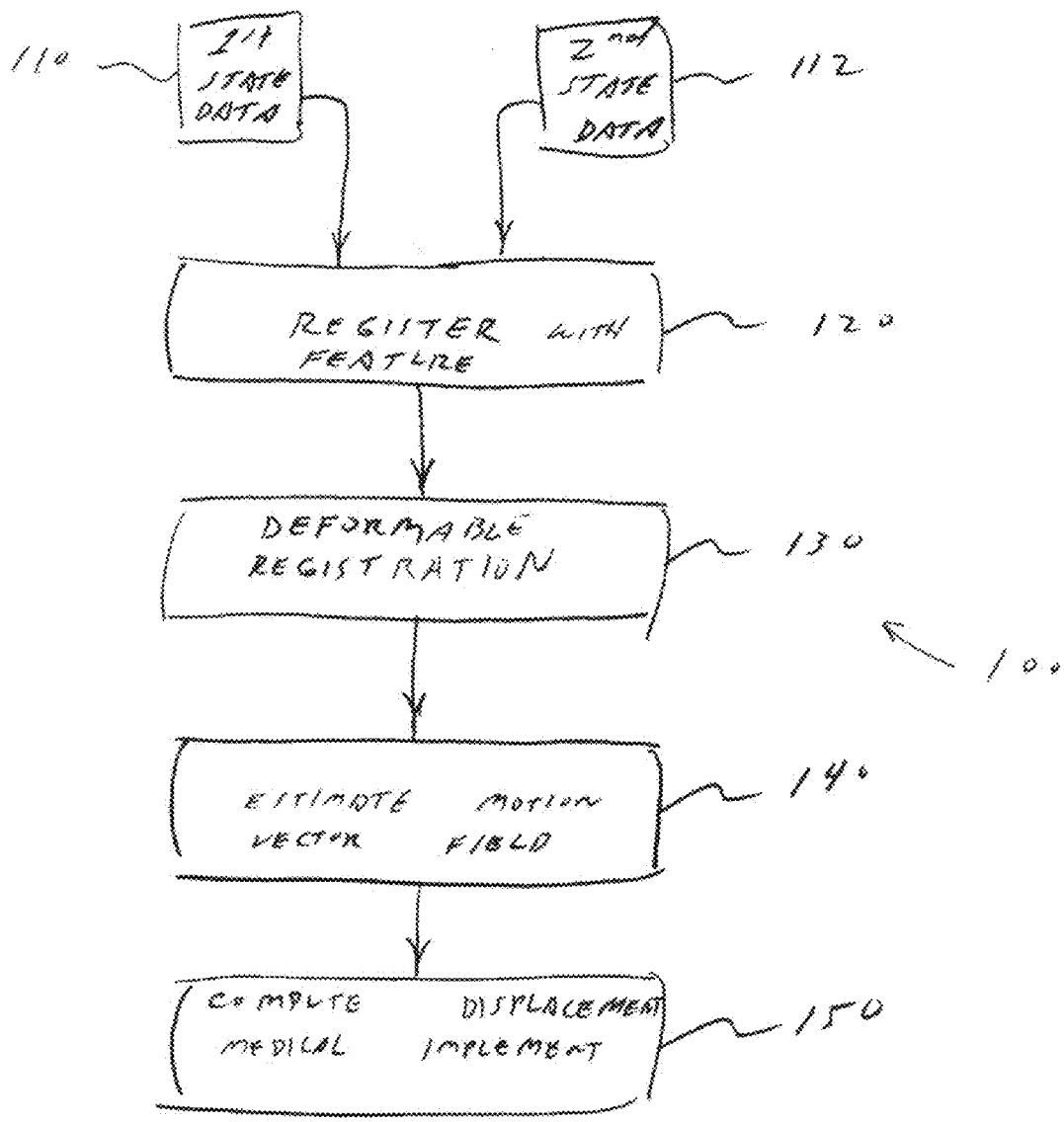
FIG. 3 is a flow chart of a method to visualize motion of a medical implement in a lung.

FIG. 3 is a flow chart illustrating an overview of a procedure 100 for assisting a physician plan a medical procedure using a medical implement. The steps shown in FIG. 3 may be carried out on a programmed computer or system and include: step 110 receiving 3D image data of the lung in a first state; step 112 receiving 3D image data of the lung in a second state; step 120 registering the 3D image data from the first state with that of the second state using a reference or anatomical feature; step 130 deforming the 3D image from the first state to match that of the second state; step 140 estimating a vector field for the local motion of the lung representing the local motion of the lung from state one to state two; and step 150 computing displacement of a virtual medical implement placed in the 3D image and subject to the motion vector field from the estimating step.

Figure 6:
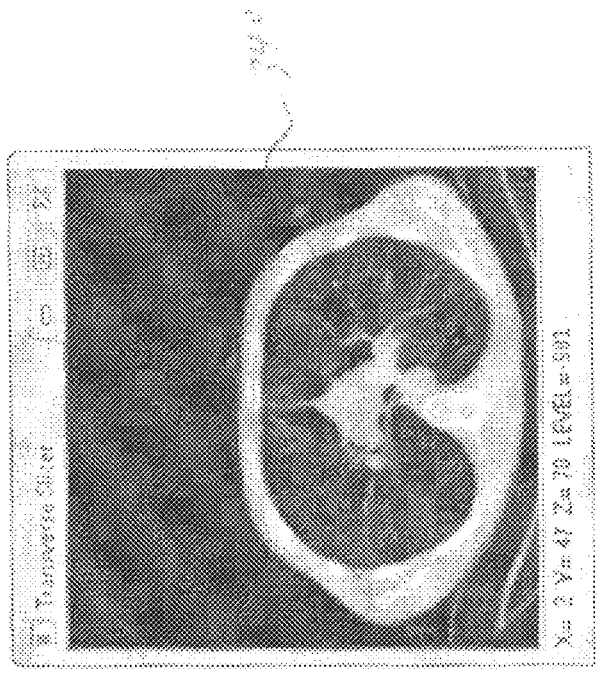

Steps 110 and 112 include receiving 3D image data of the lung in a first state and a second state. In one embodiment, receiving 3D image data of the lungs of a subject includes receiving high resolution computed tomography (HRCT) scans. FIGS. 5-6 show exemplary 2D CT image slices corresponding to inspiration and expiration of a patient, respectively.

Other acceptable data sets include without limitation MRI, 3D angiographic, and X-ray data sets. The image data may vary widely and be, for example, a 3D image file, 3D image volume, 3D image data set, or a set of 2D images of the organ from which a 3D model of the organ may be computed. An exemplary technique to determine a 3D model of the body organ is disclosed in U.S. Pat. No. 7,756,316 entitled "Method and system for automatic lung segmentation". See also, U.S. Pat. Nos. 7,889,905 and 7,756,563; and Patent Publication No. 2008/0183073 all to Higgins et al.

Also, it is to be understood that the "state" of the lung may vary widely. Non-limiting examples include: the lung at full inspiration, full expiration, partial inspiration or expiration, or anywhere in between full inspiration and full expiration; a state arising from a condition, treatment, diagnosis; a state arising from the environment, patient position, or a healthy state or control state. The second state of the lung is a state of the lung other than that of the first state. Reference to "first" and "second" is arbitrary and is not intended to limit the invention to a particular order or sequence except where such order arises from the context as a whole.

Step 120 recites registering of the 3D images with a feature such as an anatomical feature. An exemplary approach to carrying out step 120 is to rigidly align two CT images with respect to each other so that there is one-to-one correspondence between some anatomical features. Non-limiting examples of anatomical features include the spinal column or main carina.

Figure 7:
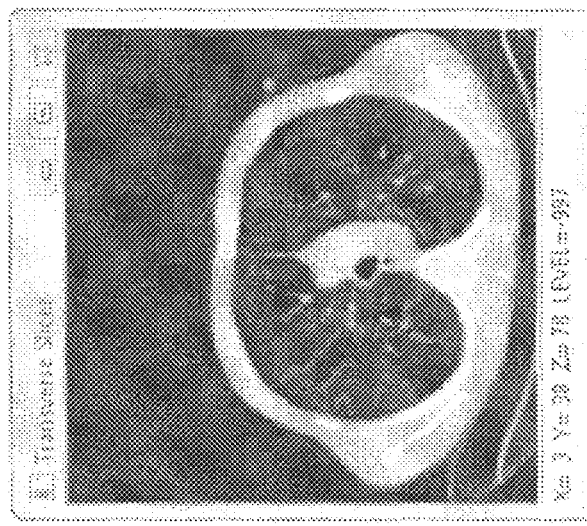
FIG. 7 is a CT image after performing a rigid alignment on the 3D image data of FIG. 5 to the slice shown in FIG. 6 such that the main carina is now aligned in both the images at the same slice.
Figure 6:
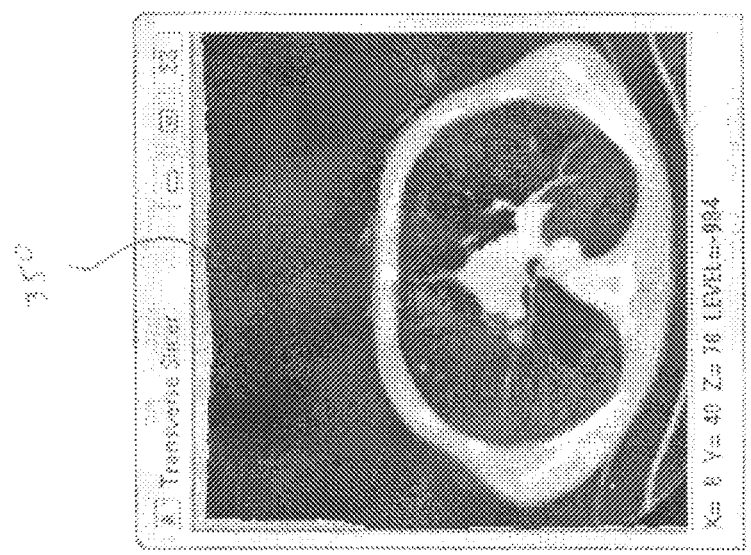
Figure 7:
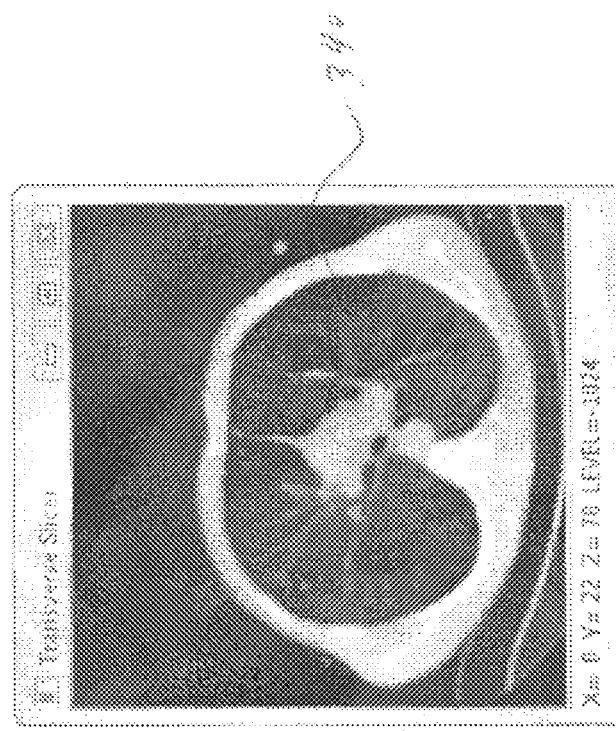

FIG. 7 shows the result after performing rigid alignment between the 3D image file corresponding to the FIG. 5 with that of FIG. 6. The image shown in FIG. 7 is rigidly aligned with that of FIG. 6, namely, the spinal column is matched. Selection of appropriate anatomical features to which rigid matching is performed provides a step in determining local tissue movement, e.g., during the respiratory cycle. As standard CT scans are often taken in the supine position, the spine has minimal deflection between different breathing states. Using the matched spines provides an anatomical reference system origin. Note, however, at this stage the lung tissue is still unmatched with respect to the local movement of tissue between the two states.

A number of approaches may rigidly register the 3D images. An approach is generating point correspondence. The point correspondence can be given manually or generated automatically. For example, the Tree Matching tool (as described in Michael Graham and William E. Higgins. "Optimal Graph-Theoretic Approach to 3D Anatomical Tree Matching," *IEEE International Symposium in Biomedical Imaging (ISBI)*, pp. 109-112, April 2006) can perform automatic correspondence of airway branches. Given the correspondence, a 3D alignment and re-sampling of the CT images places the images in the same global coordinate system. Another approach to rigidly align the two images is based on automatically aligning structures of interest. Certain structures of interest such as the spinal column are relatively fixed during the breathing cycle and may be aligned by a variety of methods. One such method is to automatically segment the structures in the images at both states, for example, using thresholding, region growing, template matching, or parametric approaches, described in U.S. Patent Publication No. 2008/0044074, filed Aug. 9, 2007 to A. Jerebko. After such images are segmented, an image-matching gradient descent algorithm can be used to determine the displacement and rotation between the segmented organs such as the Lucas-Kanade image-matching gradient descent algorithm described in B. Lucas and T. Kanade. *An iterative image registration technique with an application to stereo vision*. In Proceedings of the International Joint Conference on Artificial Intelligence, pages 674-679, 1981.

Step 130 recites deformable registration. A deformable registration moves each voxel in one of the images (e.g., source image) to match its intensity value in the other image (e.g., target image). An approach to perform this step includes minimizing a cost function (such as sum-of-squared-differences) around each voxel. Noise or structures (such as fiducial markers) may be masked out which need not be aligned prior to this registration. A suitable algorithm to perform this step is the demons algorithm, described is the Muyan-Ozcelik paper, referenced above. However, other algorithms may be used for implementation of the deformation step.

FIG. 8 shows a result after performing deformable registration between the 3D image of FIG. 7 to that of FIG. 6. The image shown in FIG. 8 is deformed such that all the voxels have been aligned. The upper edge 350 of the image evidences deformation as well.

Figure 9:
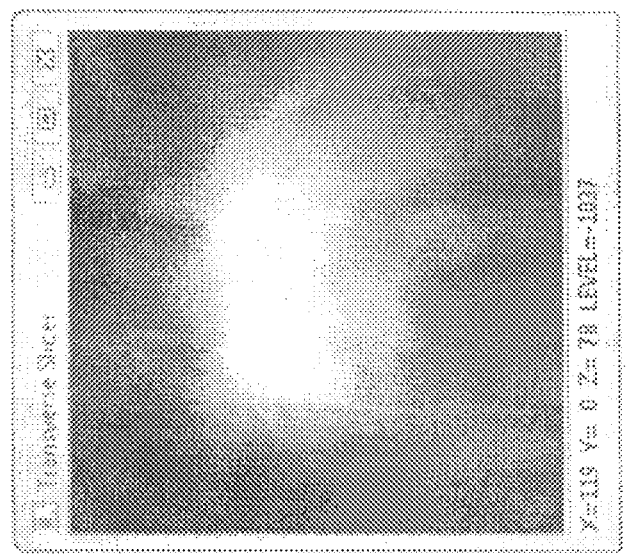
FIG. 9 is an illustration of a motion vector field of the lung corresponding to the slice shown in FIG. 6 wherein brighter areas correspond to larger breathing motion.

An output of the deformable registration step is illustrated by step 140 of FIG. 3. In particular, in this embodiment an output is the estimation or generation of a motion vector field. The motion vector field provides a direction and magnitude of each point in the 3D image of the lung indicating the movement and location between the different states of the lung. An illustration of a vector motion field corresponding to the FIG. 6 slice discussed above is shown in FIG. 9. The intensity is proportional to the breathing motion at each voxel. The brighter areas correspond to larger breathing motion.

Step 150 recites computing the displacement of a medical implement. This step is based on the motion vector field. In one embodiment, the medical implement is a fiducial, and fiducial displacement is calculated some time after initial placement.

Though not illustrated as a step, the information computed and received from the above described steps may be displayed in a wide variety of ways. In one embodiment, a virtual medical implement is superimposed onto a 3D view of the body organ. The estimated motion can be applied to animate any 2D or 3D view generated from one of the CT images. Additional markers, routes, indicia and planning information may be displayed with the images as well. The physician may then observe the estimated motion of the medical implement and the consequences of its displacement prior to performing the surgery. The physician may manipulate the virtual medical implement until determining a candidate location and or route.

Figure 4:
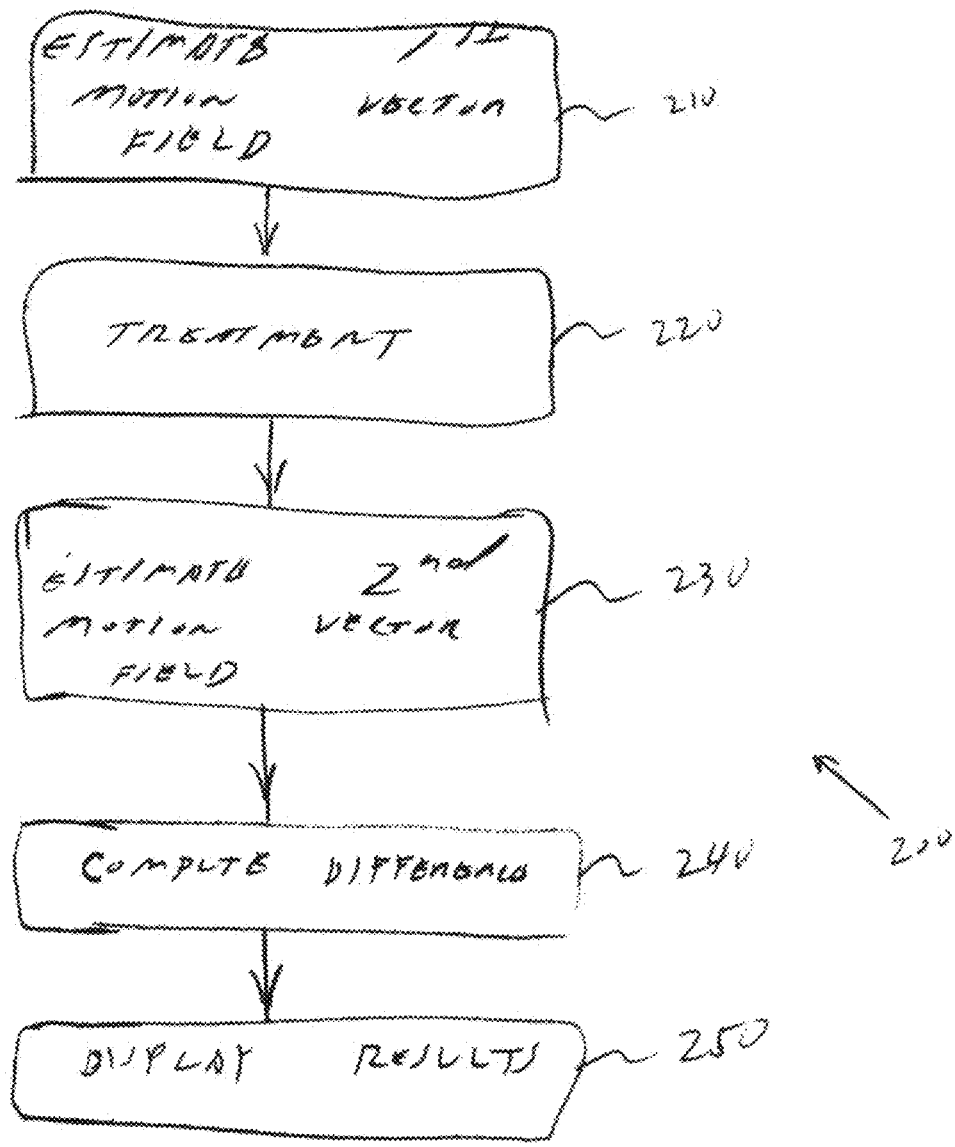
FIG. 4 is a flow chart of a method to observe the functionality of region in a lung.

FIG. 4 is a flow chart illustrating an overview of a procedure 200 to assist a physician in evaluating the efficacy of lung function or a treatment performed on the lungs.

First, step 210 recites estimating a first motion vector field. The motion vector field may be estimated on a subject as described above in connection with FIG. 3. An output from the step 210 is a first motion vector field of the lung indicating the local motion of the lung between a first state and second state such as, for example, inspiration and expiration.

Next, step 220 recites performing a treatment on the subject. For example, treatments may vary widely and include without limitation surgical treatments and interventions such as RF ablation, lung volume reduction, the placement of airway valves or stents, as well as delivery of medications, physical therapy, and conservative care treatments.

Step 230 recites estimating a second motion vector field. Step 230 is performed subsequent to the treatment step. However, in another embodiment, step 220 may be omitted and the second motion vector field is estimated after a time period, wait, bed rest, or for example a periodic or annual checkup. Step 230 is carried out the same as that described in step 210 except step 230 is performed following the treatment. The output from step 230 is a second vector motion field.

Step 240 recites computing a difference between the first motion vector field and the second vector motion field. Areas of the greatest difference may be highlighted similar to the image shown in FIG. 9. Alternatively, data may be automatically calculated by the processor to list voxels having the largest change.

Areas of greatest change may correspond to a number of conditions and regions in the lung. For example, a large change in local motion may correspond to improvement in function as would be hoped or expected in an emphysema treatment to increase the inspiration and expiration. Or perhaps, areas of largest change could correspond to the regions of the most diseased tissue (e.g., where tissue is displaced do to rapidly growing tumor). Regardless of the type of disease or diagnosis or observation, the method of the present invention provides the physician additional data to analyze the motion of the lung.

Step 250 recites displaying the results. Results and data may be displayed in a wide variety of formats and tailored to the desire of the physician. In one embodiment, a display shows the first and second motion vector fields adjacent one another. Showing the first and second motion vector fields adjacent one another is one embodiment allowing the physician to conveniently compare and contrast local lung motion prior to and after a treatment or time period. Improvement in motion before treatment and after treatment may be ascertained wherein regions of largest change are indicated in intensity, arrow length, or other indicia.

In another embodiment of the present invention, a medical analysis method for estimating a motion vector field of the magnitude and direction of local motion of lung tissue of a first subject includes a) receiving first image data of the lung of the first subject in a first state; and b) estimating the local motion of the lung of the first subject based on an atlas motion vector field.

Generating the atlas motion vector field may be carried out by creating or estimating multiple vector motion fields corresponding to multiple patients. To generate the atlas, the motion vector field is determined for a plurality of data sets of different subjects. Because subjects vary in size and shape, a regularization and registration of the motion models is required to align the different motion fields. This can be done, for instance, by matching the spines, or lungs of different patients and applying an affine warp of the motion fields of different subjects such that the motion vector fields are all brought to a regularized coordinate system.

With this model, the atlas motion vector field is applied to the first image data of the first subject to predict the motion of the lung of the first subject. While the actual motion of the lung tissue between two states in the patient may be unknown, it can be predicted from an ensemble average to estimate local motion. In this manner, only one 3D image data set is required of the subject and, using the atlas motion vector field, the local motion of the lung of the first subject is predicted.

Any of the above described method may be carried out on a system. Indeed, the invention in one embodiment is a workstation having a processor programmed to carry out any of the above described methods.

Other modifications and variations can be made to the disclosed embodiments without departing from the subject invention.

We claim:

1. A system for computing the efficacy of a surgical treatment in a region of a lung, the system comprising a processor, the processor programmed and being operable to: a) receive first image data of the lung in a first state; b) receive second image data of the lung in a second state; c) perform a rigid registration to initially align the first image data and the second image data with one another using a fixed reference feature; d) compute a change in the region in the lung between the first state and the second state based on generating a motion vector field comprising a magnitude of each point in the first image data and second image data of the lung indicating movement and location between the first state and second state and direction of local motion of lung tissue between the first state and second state and computed independent of the fixed reference feature defined in the performing a rigid registration step; e) determine efficacy of the surgical treatment based on said change in the region in the lung; and indicate the change in the region in the lung between the first state and the second state.

2. The system of claim 1 wherein the processor is operable to perform a deformable registration to deform: i) the first image data of the lung to match the second image data of the lung, and/or ii) the second image data of the lung to match the first image data of the lung.

3. The system of claim 1 wherein the processor automatically selects the fixed reference feature from a set consisting of the ribs and spine.

4. The system of claim 3 wherein the processor computes displacement of a 3D location of a candidate medical implement based on the motion vector field.

5. The system of claim 4 further comprising a display, and displaying the displacement of the medical implement.

6. The system of claim 5 wherein the motion vector field corresponds to respiratory motion of the lung.

7. The system of claim 1 wherein the change in the region corresponds to tissue displacement.

8. The system of claim 1 wherein the step of indicating is performed by arrow length or intensity.

9. A method for computing the efficacy of a surgical treatment in a region of a lung, the method comprising the steps of: a) receiving first image data of the lung in a first state; b) receiving second image data of the lung in a second state; c) performing a rigid registration to initially align the first image data and the second image data with one another using a fixed reference feature; d) computing a change in the region in the lung between the first state and the second state to determine efficacy of the surgical treatment based on generating a motion vector field comprising a magnitude of each point in the first image data and second image data of the lung indicating movement and location between the first state and second state and direction of local motion of lung tissue between the first state and second state and computed independent of the fixed reference feature defined in the performing a rigid registration step; and e) indicating the change in the region in the lung between the first state and the second state.

10. The method of claim 9 wherein the first state is observed prior to the surgical treatment, and the second state is an efficacy state arising from the surgical treatment.

11. The method of claim 9 wherein the change in the region corresponds to tissue displacement.

12. The method of claim 11 further comprising receiving a 3D location of a candidate medical implement.

13. The method of claim 12 further comprising computing displacement of the candidate medical implement based on the motion vector field.

14. The method of claim 13 wherein the motion vector field corresponds to respiratory motion of the lung.

15. The method of claim 9 further comprising, and based on step (c), performing a deformable registration to deform: i) the first image data of the lung to align the second image data of the lung, and/or ii) the second image data of the lung to align the first image data of the lung.

16. The method of claim 11 wherein the step of indicating is performed by arrow length or intensity.

17. A medical method for computing the efficacy of a surgical treatment in a region of a lung, the method comprising the steps of: a) receiving first image data of the lung in a first state; b) receiving second image data of the lung in a second state; c) rigidly aligning the first image data and the second image data with one another based on a rigid anatomical structure; d) computing a change in the region in the lung between the first state and the second state to determine efficacy of a surgical treatment based on generating a motion vector field comprising a magnitude of each point in the first image data and second image data of the lung indicating movement and location between the first state and second state and direction of local motion of lung tissue between the first state and second state and computed independent of the rigid anatomical structure defined in the rigidly aligning step; and e) indicating the change in the region in the lung between the first state and the second state.

18. The method of claim 17 wherein the rigid anatomical structure is selected from a set consisting of the ribs and spine.

19. The method of claim 17 further comprising displaying areas of greatest difference in highlighted form.

20. The method of claim 19 wherein the first state is observed prior to the surgical treatment, and the second state is an efficacy state arising from the surgical treatment.

21. The method of claim 20 wherein the surgical treatment removes a region of interest.

22. The method of claim 21 wherein the surgical treatment comprises ablation.

23. The method of claim 21 further comprising deforming i) the first image data of the lung to match the second image data of the lung, and/or ii) the second image data of the lung to match the first image data of the lung, wherein the deforming is based on the rigidly aligning step.

24. The method of claim 17 wherein the step of indicating is performed by arrow length or intensity.

25. The method of claim 17 wherein the change in the region corresponds to tissue displacement.

\* \* \* \* \*